(12) United States Patent
Gord et al.

(10) Patent No.: US 6,458,093 B1
(45) Date of Patent: *Oct. 1, 2002

(54) APPARATUS FOR INSUFFLATING GAS INTO A CORPOREAL CAVITY OF A HUMAN OR ANIMAL BODY

(75) Inventors: John C. Gord, Venice, CA (US); Eric M. Jones, Southbridge, MA (US); Juergen Kraft-Kivikoski, Radolfzell (DE)

(73) Assignee: Storz Endoskop GmbH (CH)

( * ) Notice: Subject to any disclaimer, the term of this patent is extended or adjusted under 35 U.S.C. 154(b) by 29 days.

This patent is subject to a terminal disclaimer.

(21) Appl. No.: 09/824,480

(22) Filed: Apr. 2, 2001

(Under 37 CFR 1.47)

Related U.S. Application Data

(63) Continuation-in-part of application No. 09/077,250, filed on Feb. 5, 1999, now Pat. No. 6,238,365.

(51) Int. Cl.$^7$ .............................................. A61M 37/00
(52) U.S. Cl. ........................................................ 604/26
(58) Field of Search ............................. 604/23, 26, 30, 604/39, 24, 67, 85, 118, 120, 123, 124, 140; 600/560

(56) References Cited

U.S. PATENT DOCUMENTS

| 4,874,362 A | 10/1989 | Wiest et al. ................. 604/26 |
| 5,549,546 A | * 8/1996 | Schneider et al. ............ 604/26 |
| 5,800,381 A | * 9/1998 | Ognier ........................ 604/26 |
| 6,238,365 B1 | 5/2001 | Gord et al. .................... 604/26 |

FOREIGN PATENT DOCUMENTS

| DE | A-30 00 218 | 1/1980 |
| DE | C-36 11 018 | 3/1986 |
| DE | A-42 19 859 | 6/1992 |
| EP | B-0 169 972 | 4/1985 |
| EP | 0 489 716 A1 | 6/1992 |
| WO | WO 95/23006 | 8/1995 |

\* cited by examiner

Primary Examiner—Anhtuan T. Nguyen
(74) Attorney, Agent, or Firm—St. Onge, Steward, Johnston & Reens LLC

(57) ABSTRACT

A device for insufflating gas into a corporeal cavity of a human or animal body has a connection for a gas source, a measuring unit provided with sensors for the fill gas pressure and the fill gas flow, which are disposed outside said corporeal cavity, and a control unit, to which the output signal of the sensors are applied, and which triggers a pressure regulator which reduces the fill pressure of the gas source to a pre-set insufflation pressure, and a flow regulator which regulates the fill gas flow to a pre-set desired gas flow value in accordance with first a square function, and then, after reaching the preset flow rate, in accordance with a linear function.

21 Claims, 3 Drawing Sheets

APPARATUS FOR INSUFFLATING GAS INTO A CORPOREAL CAVITY OF A HUMAN OR ANIMAL BODY

RELATED APPLICATIONS

This application is a continuation-in-part of U.S. patent application Ser. No. 09/077,250, filed Feb. 5, 1999, now U.S. Pat. No. 6,238,365.

FIELD OF THE INVENTION

The present invention relates to a device for insufflating gas, such as $CO_2$, into a corporeal cavity of a human or animal body and including a source of gas and a control unit regulating the gas pressure and gas flow through a needle during an endoscopic surgery.

BACKGROUND OF THE INVENTION

A good number of embodiments of generic type devices for insufflating gas are known. With regard to this, reference is made to DE-A-30 00 218, EP-B-O 169 972, DE-C-36 11 018, U.S. Pat. No. 4,874,362 and DE-A-42 19 859. Moreover, reference is explicitly made to these printed publications for the explanation of all details not made more apparent herein.

A typical device for insufflating gas 10 into a corporeal cavity 30, as shown in FIG. 3, possesses a connection for a gas source 32, such as a pressure cylinder, and the capability of setting the gas pressure and the gas flow. For this purpose, the known devices are provided with, for example, a pressure and the gas flow sensors. Also, the known devices are provided with, a pressure/gas flow regulator 34 which reduces the pressure of the gas source to a insufflation pressure (desired gas pressure), which can be set, of typically between 0 and 50 mm Hg, and a flow regulator which sets the gas flow to a value (desired gas flow).

In the generic devices described in the aforementioned printed publications, the gas pressure or the gas flow can not only be controlled, but they are also regulated. For this purpose, these devices are provided with a measuring device having sensors for the actual gas pressure 36 and the actual gas flow 38, and with a control unit 40 to which the output signals from these sensors are applied and which controls the pressure regulator and the flow regulator 34, as shown in FIG. 3.

However, a problem with the known devices for insufflating gas into a corporeal cavity is measuring the gas pressure, because it is usually impossible or only with great effort to measure the gas pressure directly inside the corporeal cavity. Due to the streaming gas and the drop in pressure (i.e. generated thereby), measuring the pressure outside the corporeal cavity leads to a measuring error, which cannot be readily tolerated in medical applications.

Therefore, it is proposed in that order to measure the "static" gas pressure P, to reduce the gas flow Q to the value 0 and to measure the gas pressure when the gas flow actually reaches the value 0 "statically". With regard to this, reference is made to FIG. 6 of U.S. Pat. No. 4,874,362 and the respective specification. Although this method has the advantage that it permits relatively accurate measurement of the gas pressure, it has the disadvantage that it does not permit an even relatively constant gas supply.

Furthermore, it has been proposed to calculate the pressure actually prevailing in the corporeal cavity from the output signal of the sensor while taking into account the flow resistance of the tube instrument and the insufflation instrument, such as a Verres needle, between the pressure sensor and the corporeal cavity whose pressure is to be determined.

However, in practice determining the flow resistance and the drop in pressure between the pressure sensor and the corporeal cavity has proven difficult.

SUMMARY OF THE INVENTION

The invented device is distinguished by the fact that, the control unit calculates the drop in pressure $P_{drop}$ between the location of the pressure sensor and the corporeal cavity and therefore the actual gas pressure $P_{abd}$ inside the corporeal cavity (intraabdominal pressure), as a function of the gas pressure $P_{fill}$ measured outside the corporeal cavity and the measured gas flow Q. The calculated drop in pressure $P_{drop}$ as the function of Q is less or at the most equals the actual drop in pressure. The control unit calculates the gas pressure $P_{abd}$ in an event and/or time controlled manner during normal insufflation and regulates the insufflation on the basis of the calculated gas pressure $P_{abd}$.

An object of the present invention is to further develop a device for insufflating gas into a corporeal cavity of a human or animal body in such a manner that the drop in pressure between the pressure sensor and the corporeal cavity and therefore the pressure inside the corporeal cavity can be determined as accurately as possible while ensuring highest possible patient safety.

The present invention is based on a generic device for insufflating gas into a corporeal cavity of a human or animal body and further improves this device according to the present invention as follows:

For calculating the drop in pressure $P_{drop}$ between the site of the pressure sensor and the corporeal cavity, whose pressure as the actual gas pressure $P_{abd}$ (intraabdominal pressure) is the relevant pressure, the control unit uses one of a plurality of simple functions of the gas pressure $P_{fill}$ measured outside the corporeal cavity and of the measured gas flow Q. On the basis of these functions, the calculated pressure drop $P_{drop}$ as the function of Q is less than or at most equals the actual pressure drop. Furthermore, the control unit continuously calculates the event and/or time controlled gas pressure $P_{abd}$ during the normal insufflation and regulates insufflation on the basis of the calculated gas pressure $P_{abd}$ Thus, unlike prior art systems, no single complicated mathematical function is used to express the variation in pressure drop from the gas flow rate throughout the entire range of values of gas flow rate. Instead, the function to be employed is selected from a plurality of functions based upon the flow rate. Thus, in the example more fully discussed below, a function having a simple square dependency on the pressure drop of the gas flow rate is used only at low gas flow rates, while a function having a simple linear dependency is used only at high gas flow rates. Thus, to cover the entire range of gas flow rates, either one function or the other is used, as expedient.

Based on the invention method, the intraabdominal pressure prevailing inside the corporeal cavity is not underestimated at any time. As the intraabdominal pressure prevailing inside the corporeal cavity is continuously determined, contrary to the known devices in which the intraabdominal pressure is determined at relatively large time intervals, a too high a pressure can never occur inside the corporeal cavity.

Tests have shown that at usual gas flows of up to 20 liter/min, as are used in medical insufflation procedures, it is sufficient to employ two functions for determining the drop in pressure, which are drawn upon for certain flow rates.

Thus, according to one aspect of the Invention, it is preferred that when the flow rates are less than a specific flow rate $Q_{ums}$, a square dependency of the pressure drop on the flow rate is utilized. At flow rates that are greater than this specific flow rate, it is preferred if a linear dependency of the drop in pressure on the flow rate is utilized. Using these two functions ensures that the calculated drop in pressure is always less than or at most equals the actually occurring drop in pressure between the measurement site and inside the body, so that a too high a pressure can never occur inside the body cavity.

The invented principle for determining the pressure drop in the tubes and in the other instruments in dependency on the flow rate can be applied in a great variety of devices.

For instance, it can be applied in devices in which the control unit determines the constants $K_1$ and $K_2$ while taking into account the flow resistance of the insufflation instruments. In particular, it is conceivable that these constants are calculated on the basis of expectancy values and the respective length of the tube instrument as well as of the employed instrument.

However, it is particularly advantageous that according to another aspect of the invention, in order to determine the constants $K_1$, and $K_2$, the control unit determines the values $P_{fill}$ and Q (to be utilized in the equation in the resolution of these equations for the constants $K_1$, and $K_2$) at essentially constant gas flow Q and the value $P_{abd}$ in a gas flow "distinctly reduced" compared to normal gas flow. The flow can be lowered to "zero" or to a value differing distinctly from zero, as described in the not prepublished PCT/DE95/00756.

This application describes that while the pressure is being measured, the actual gas flow is set at a value between 10 and 40% of the desired gas flow.

In both instances, the gas flow prior to reduction, that is the gas flow during "normal" insufflation, is taken for correcting the pressure value of the gas flow measured by the pressure sensor.

As the flow resistance of the insufflation instrument may change, by way of illustration due to an unintended bend in the tubing, according to still another aspect of the invention, it is preferred that the control unit uses the constants $K_1$, and $K_2$ for calculating the intraabdominal pressure in the corporeal cavity only for the next cycle, i.e. until the next drop in flow. Therefore, in the preferred embodiment, the control unit calculates the constants $K_1$, and $K_2$ anew for each cycle from values determined in the preceding cycle.

The invention also discloses a method of determining the value of the flow or the flow rate $Q_{ums}$ at which the control unit switches between linear and square dependency of the drop in pressure in the flow rate. The value of the flow rate at which it is switched is determined by the point of intersection of the linear and the square dependency of the drop in pressure $P_{drop}$ at the flow rate Q for each determined constant $K_1$ and $K_2$.

The measurement principle of the invented device can be applied in a great variety of devices for insufflation of gas in corporeal cavities. It is particularly advantageous to use the measuring principle in devices which can also generate high flow rates (>10 l/min.), because in devices of this type, the influence of the flow rate is especially great due to the large variation of the flow rate.

If, for instance, a maximum flow rate of 30 l/min. and an interval common in the state of the art of approximately 2 seconds between successive measurements of the pressure inside a corporeal cavity at a gas flow rate reduced to 0 is assumed, in the case of an especially small corporeal cavity (small patients, children), which in this case is usually less than 3 liters, there is a considerable rise in pressure, because a gas volume of one liter is transported into the corporeal cavity within 2 seconds.

The invented device extrapolates the pressure inside the body continuously by means of the approximated plurality of utilized pressure drop characteristic curves between the respective pressure measuring points at a low flow or a flow of 0 permitting an event-controlled premature break-off of the insufflation phase. Therefore, unlike in the state of the art in which pressure measurement occurs time-controlled, it is not necessary to lower the flow after a fixed time interval in order to be able to measure the intraabdominal pressure.

In this way, a constant or at least an approximately constant gas flow over longer periods of time is provided. Due to the, compared to the state of the art, reduced fluctuations of the gas flow, the condition dependencies change less than in the state of the art. Nonetheless, accurate pressure determination is possible.

In this context, it is advantageous if the control unit generates an alarm if the flow sensor measures a gas flow value of 0, because this value may indicate a defect in the instrument.

Furthermore, an evacuation valve may be located at the proximal part of an instrument inserted in the corporeal cavity is provided in an as such known manner for limiting the intraabdominal pressure.

Therefore, the control unit closes the evacuation valve at intervals duration of which depends on the intraabdominal pressure. Thus, these intervals of the insufflation do not have to be fixed.

Furthermore, it is preferred that a vacuum pump is provided, also in a known manner, for enhancing evacuation.

The invented design, in which the control unit continuously extrapolates thepressure inside the body, permits controlling the vacuum pump in dependence on the intraabdominal pressure.

Moreover, the aforementioned invented design permits using not only an "on/off valve", but also a proportional valve the position of which the control unit regulates in dependence on the pressure inside the body.

Another preferred application of the invented measuring principles given in devices in which a heating device is provided in an as such known manner, whichheats the to-be-insufflated gas to a predetermined temperature. This heating device may, by way of illustration, be provided inside on the tubing between the actual device, i.e. between the control device and the instrument or instruments inserted into the body. With regard to the latter preferred embodiment, which is especially advantageous, reference is made to WO 94/28952.

In the case of a device in which the insufflation gas is heated it is especially advantageous if the control unit sets the gas pressure and the gas flow while taking into account the predetermined gas temperature. This reduces the time span until the desired value is reached; moreover the measured value can be corrected according to the set temperature so that the desired/actual setting is improved.

In addition, the invented measuring principle permits another measurement, notably determination of the characteristic flow value of the tubing, i.e. in particular the insufflation tube and the insufflation channel of the endoscopic instruments.

For this purpose the control unit determines the characteristic flow value of the tubing to the corporeal cavity from the gas pressures measured by the pressure sensor at least two different flow values. With the characteristic flow value, the actual value of the pressure inside the corporeal cavity can also be calculated from the value of the gas pressure measured outside the body.

This method has the advantage that it permits exact determination of the, flow-dependent, characteristic flow value without removing the instrument out of the body and therefore independent calculation of the pressure inside the corporeal cavity and the instrument for additional control of the values determined according to the present invention.

For determination of the characteristic flow value, it is necessary to measure at least two difference flow values; measuring at more than two flow values permits increasing precision by redundancy comparison.

Furthermore, the invented device does not require provision of a second tube for measuring the pressure inside the corporeal cavity.

For insufflating gas into the corporeal cavity, endoscopic instruments, such as a Verres needle, can be provided on which the sensors for gas pressure and gas flow are disposed outside the corporeal cavity.

In any event, the invented device has the advantage that, compared to the known devices described in older patent applications, it offers excellent pressure constancy with greater accuracy of pressure measurement although the gas flow may vary drastically.

The remaining construction of the invented device may correspond to the construction of known devices for insufflating gas into a corporeal cavity with regard to the connection for a gas source, to a measuring device and to the control unit provided, by way of illustration, with a microprocessor. In particular, the pressure regulator and the flow regulator can be combined in one component.

The invention and its particular features and advantages will become more apparent from the following detailed description considered with reference to the accompanying drawings.

BRIEF DESCRIPTION OF THE DRAWINGS

The present invention is made more apparent in the following using a preferred embodiment with reference to the accompanying drawings, in which.

DETAILED DESCRIPTION OF THE INVENTION

Figure 1:
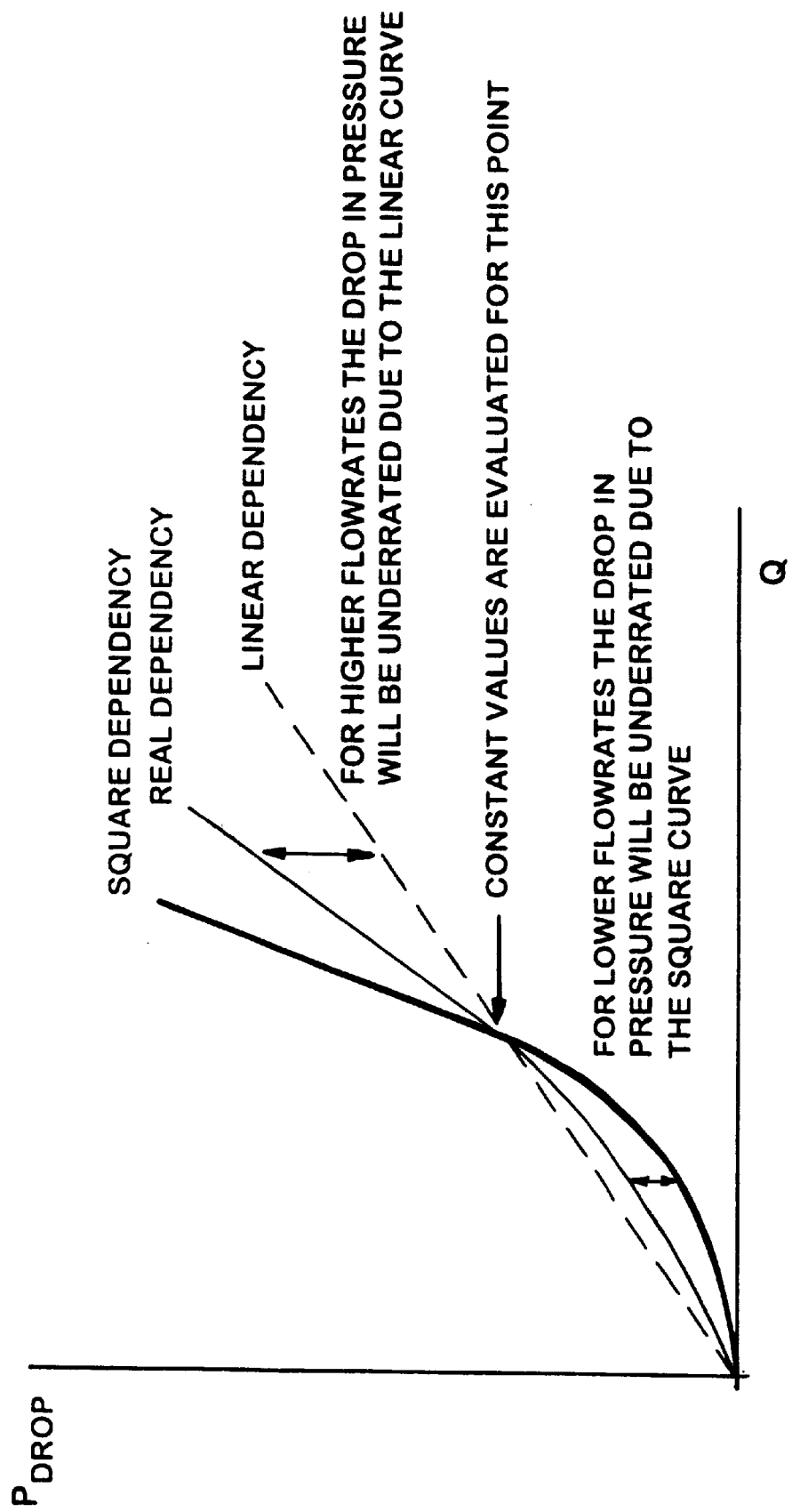
FIG. 1 illustrates the real dependency of the drop in pressure on the flow rate.

During an insufflation procedure, when a gas is passed through a line into a corporeal cavity, the pressure of the gas inside the cavity must not become too large. It is possible to measure and monitor the gas pressure and the gas flow in the line at a position outside the cavity. However, it is difficult to measure and monitor the pressure of the gas in the cavity. The pressure of the gas flowing past the position of measurement outside the cavity is subject to a pressure drop along the line into the cavity owing to the resistance encountered by the gas flow on its way through the line.

The objects of the present invention, as set forth above, are achieved in accordance with the following principles.

During an insufflation the pressure inside the corporeal cavity $P_{abd}$ is equal to the difference between the pressure as measured at the position in the gas line outside the corporeal cavity and the pressure drop $P_{drop}$ in the line between the position of pressure measurement and the cavity. This pressure drop $P_{drop}$ is known to vary with the gas flow Q in a non-linear manner, as shown by the solid line curve in FIG. 1, the variation being determined by the type and temperature of the gas used and various instrument parameters.

As the pressure drop $P_{drop}$ can be expressed only as a complicated mathematical function of the gas flow Q as measured in the line outside the cavity, simple mathematical functions are used for approximately calculating the pressure drop $P_{drop}$ at any particular value of the gas flow Q.

For example, the pressure drop $P_{drop}$ may be assumed to vary linearly with the gas flow Q along the entire range of gas flow values, i.e., the pressure drop $P_{drop}$ is given by the function K,×Q, where K, is a constant and Q is the gas flow. In this case, at low values of Q the calculated pressure drop $P_{drop}$ will be higher than the actual the pressure drop, and at high values of Q the calculated pressure drop $P_{drop}$ will be lower than the actual pressure drop. However, as it is desirable not to underestimate the pressure inside the cavity $P_{abd}$, it is desirable to use pressure drop values which are on the low side for calculating the cavity pressure $P_{abd}$ and controlling the insufflation (i.e., cavity pressure $P_{abd}$= measured pressure $P_{fill}$–pressure drop $P_{drop}$). Therefore it is desirable to use the linear relationship only at high values of Q.

On the other hand, the pressure drop $P_{drop}$ may be assumed to vary with the square of the gas flow Q, i.e., the pressure drop $P_{drop}$ equals K2×Q², where K2 is another constant. In this case, at low values of Q the calculated pressure drop $P_{drop}$ will be lower than the actual pressure drop, and at high values of Q the calculated pressure drop $P_{drop}$ will be higher than the actual pressure drop. Here it is desirable to use the square relationship only at low values of Q.

The control unit for calculating the pressure drop $P_{drop}$ and hence the pressure inside the cavity $P_{abd}$, is adapted to switch over from using one function to using the other function according to the measured actual value of the gas flow Q.

Of course, the variation of the actual pressure drop with the gas flow Q may be approximated by other functions than the above two, and there may be more than two functions, each being used only within a particular range of values of the gas flow Q.

The functions used and the values of any constants therein (i.e., the values of K, and K2 used in the simple case above), may be predetermined by involved experiments.

However, according to the invention, the control unit can be adapted to predetermine the functions. In the above simple case it does this by measuring the gas pressure and the gas flow when constant during an insufflation cycle, and then measuring both again at the end of the cycle, when the gas source is shut off from the gas line and the gas flow is zero.

From the first measurement the following relationships are obtained:

$$P_{abd} = P_{fill} - K_1 \times Q \qquad (1)$$

$$P_{abd} = P_{fill} - K_2 \times Q^2 \qquad (2)$$

From the second measurement the following relationship is obtained:

$$P_{abd}=P_{fill} (Q \text{ being zero}) \quad (3)$$

From the equations (1) and (3) the value of $K_1$, can be calculated, and from the equations (2) and (3) the value of $K_2$ can be calculated. The calculated values of $K_1$ and $K_2$ are stored by the control unit and used in the form of the respective linear or square functions for calculating the pressure drop $P_{drop}$ in the next insufflation cycle, as follows:

$$P_{drop}=K_1 \times Q, \text{ or } P_{drop}=K_2 \times Q^2.$$

Only one of the two functions is selected and used by the control unit in the next insufflation cycle according to whether the gas flow value Q is high or low. From the pressure drop $P_{drop}$ as calculated using the selected function, the cavity pressure $P_{abd}$ is calculated and used to control further insufflation, the calculated cavity pressure $P_{abd}$ always being on the high side for reasons of safety.

A more detailed exemplary illustration follows.

In the case of electronic insufflators, the gas flow is usually reduced to zero in order to be able to measure the intraabdominal pressure. If the pressure is measured at a gas flow of unequal to zero, this value always represents the insufflation pressure which comprises the intraabdominal pressure and the drop in pressure of the supply systems. Especially with modern "hi-flow" insufflators and small connected volumes there is a danger that a great overpressure can set in between two time points for measuring the intraabdominal pressure. The invented device permits avoiding these overpressure conditions.

Measurements with different tube configurations have shown that the drop in pressure can basically assume different courses depending on the gas flow. This is shown in FIG. 1: the continuous curve in FIG. 1 depicts a typical real dependency of the drop in pressure $P_{drop}$ on gas flow Q. In order to approximate this real curve, the control unit employs:

at flow rates less than a specific flow rate $Q_{ums}$, a square dependency of the drop in pressure $P_{drop}$ on the flow rate Q:

$$P_{abd}=P_{fill}-P_{drop}=P_{fill}-K_2 * Q^2$$

and at flow rates greater than the specific flow rate $Q_{ums}$, a linear dependency of the drop in pressure $P_{drop}$ on the flow rate Q:

$$P_{abd}=P_{fill}-P_{drop}=P_{fill}-K_1 * Q.$$

The square dependency is indicated by the dotted line curve and the linear dependency by the broken line curve in FIG. 1.

Factors $K_1$ and $K_2$ are, i.e. dependent on the type of gas, the temperature of the gas, the diameter and the length of the instruments.

The intraabdominal pressure $P_{abd}$, which is given by the insufflation pressure $P_{fill}$ minus the drop in pressure $P_{drop}$ can also be calculated if $P_{fill}$ and the gas flow Q are measured and the system is known from the factor k:

$$P_{abd}=P_{fill}-K_1 * Q \text{ for the linear course of the curve.}$$

$$P_{abd}=P_{fill}-K_2 * Q_2 \text{ for the square course of the curve.}$$

Conversely, the two constants $K_1$, and $K_2$ can be calculated using the same formulas by the resolution of the equations for K. However, $P_{abd}$ and $P_{fill}$ cannot be measured at the same time.

Therefore, the two constants are recalculated after every cycle by the control program of the control unit. For this purpose values are used for $P_{fill}$ and Q that were stored during the preceding cycle.

Figure 2:
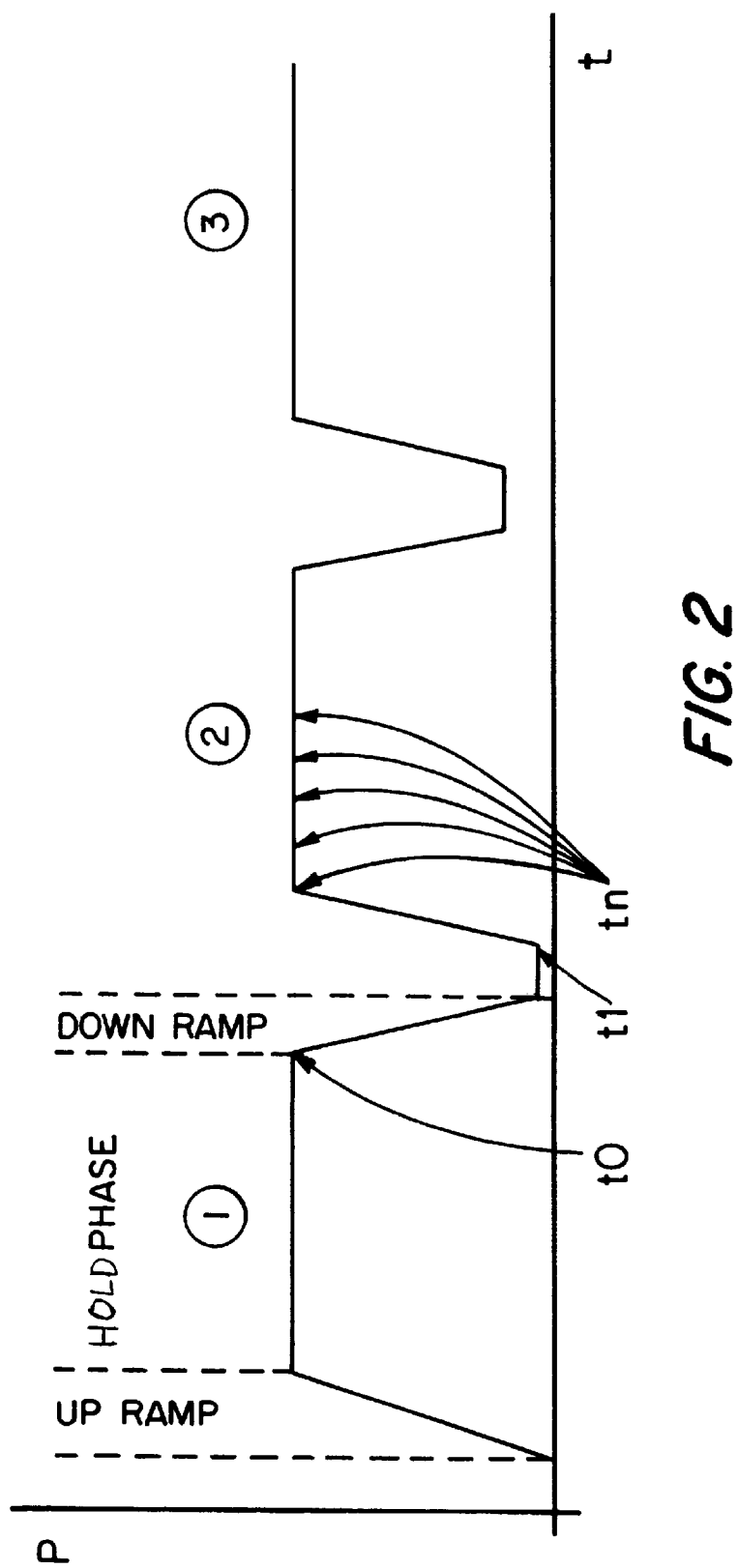
FIG. 2 illustrates a pressure/time diagram for the invented device.
Figure 3:
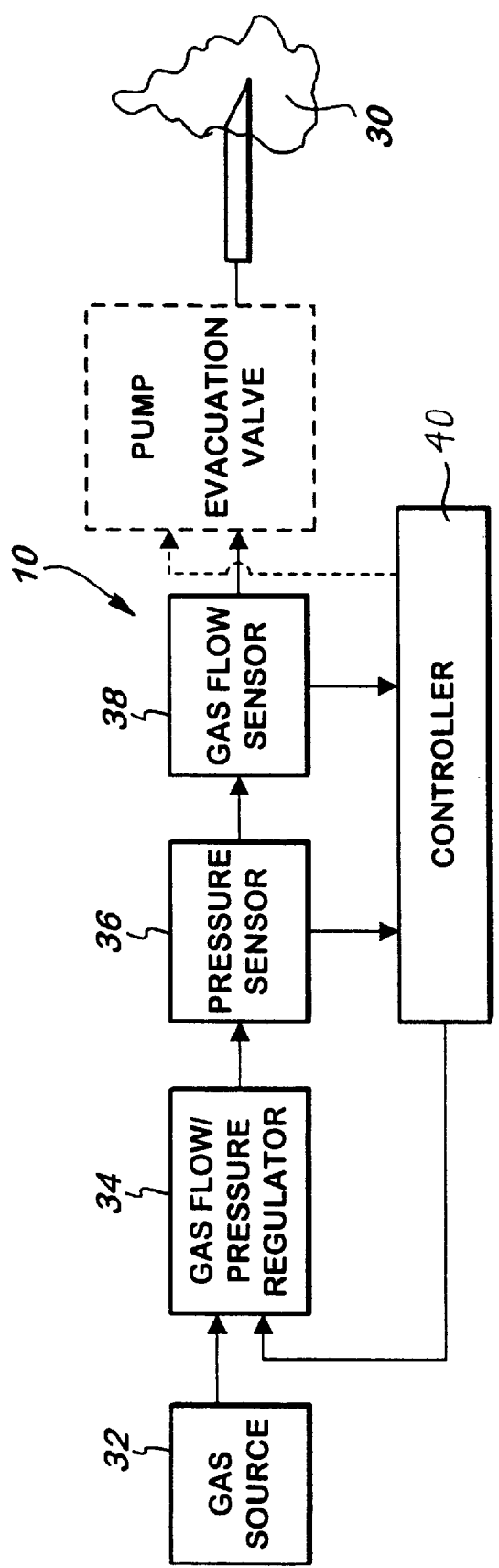
FIG. 3 is a diagrammatic view of the typical insufflator known in the prior art.

FIG. 2 shows the temporal course of the precalculation for the pressure in a pressure/time diagram.

At the point of time to, the values $P_{fill}$ and Q required for calculating the constants are stored. At the point of time tl, the measured pressure value equals $P_{abd}$, because the gas flow Q=0. At this point in time, all the required parameters are available so that the two constants $K_1$ and $K_2$ can be calculated.

With these constants and the respective current pressure $P_{fill}$, the intraabdominal pressure $P_{abd}$ is calculated (continuously) at points of time. If this calculated value is more than a threshold safety margin (for example 2 mm Hg) greater than the desired value, the insufflation phase is interrupted and the down ramp is started. The precalculation for the pressure is conducted in each main program cycle as long as the device is in the hold phase.

At the end of the hold phase of the filling cycle 2, the values $P_{fill}$ and Q are stored again and the procedure is repeated.

In the following, a numerical example is provided without any invention of limiting the scope or spirit of the general concepts:

With an insufflation instrument having a Verres needle having an internal diameter of approximately 3 mm, according to the present invention usual up to a gas flow rate of 4.5 liters/min. A square dependency of the pressure drop is assumed for the flow rate and at higher flow rates a linear dependency is assumed. With an entire length of the tubing and of the insufflation instrument of approximately 2 m, the drop in pressure is approximately 16 mm Hg at a $CO_2$ flow rate of 4.5 liters/min. These values may, of course, vary depending on the length of the instruments and the internal diameter.

A device is able to be constructed like known devices with regard to the connection for the gas source, to the measuring device with sensors for the actual gas pressure and the actual gas flow, and to the control unit to which the output signals of the sensors are applied, which signals triggering the pressure regulator and the flow regulator, with only the cycle program of the microprocessor or of the PC, which controls the functions of the device, being adapted to the invented principle. For this reason, a detailed description of the individual "hardware components" is forfeited.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A device for insufflating gas into a corporal cavity of a body, having:
   a connection for a gas source;
   a measuring unit provided with sensors, disposed outside the corporal cavity, for generating signals indicating a fill gas pressure $P_{fill}$ measured outside the corporal cavity and a measured fill gas flow Q;
   a control unit, to which the sensor signals are applied;
   a pressure regulator responsive to said control unit to regulate the fill gas pressure $P_{fill}$ to a desired insufflation pressure; and
   a flow regulator responsive to said control unit to regulate the fill gas flow Q to a desired flow value;

characterized by the fact that said control unit during normal insufflation repeatedly calculates in an event or time controlled manner a drop in pressure $P_{drop}$ between the location of the pressure sensor and said corporeal cavity using a selected function of the gas pressure $P_{fill}$ measured outside the corporeal cavity and the measured gas flow Q;

that said control unit selects said function in each case from a plurality of predetermined functions as being the function which yields a calculated pressure drop $P_{drop}$ which is smaller or at most equal to the actual pressure drop; and that said control unit calculates from the calculated drop in pressure $P_{drop}$ the gas pressure $P_{abd}$ inside said corporeal cavity and regulates the insufflation according to the calculated gas pressure $P_{abd}$.

2. A device according to claim 1, characterized by the fact that at flow rates less than a specific flow rate $Q_{ums}$, said control unit utilizes a square dependency of the drop in pressure $P_{drop}$ on the flow rate Q expressed by the equation:

$$P_{abd}=P_{fill}-P_{drop}=P_{fill}-K_2*Q_2$$

and at flow rates greater than said specific flow rate $Q_{ums}$, said control unit utilizes a linear dependency of the drop in pressure $P_{drop}$ on the flow rate Q $$P_{abd}=P_{fill}-P_{drop}=P_{fill}-K_1*Q.$$

3. A device according to claim 2, characterized by the fact that said control unit determines said constants $K_1$, and $K_2$ while taking into account the flow resistance of the insufflation instrument.

4. A device according to claim 2, characterized by the fact that, in order to determine the constants $K_1$, and $K_2$, said control unit determines the (to be-utilized) values $P_{fill}$ and Q at an essentially constant gas flow Q and said value $P_{abd}$ at a gas flow which is reduced to a small value or to zero.

5. A device according to claim 4, characterized by the fact that said control unit triggers said flow regulator in such a manner that said small value of said gas flow amounts to approximately between 10% and 40% of the desired gas flow during pressure measurement.

6. A device according to claim 4, characterized by the fact that said control unit only utilizes said constants $K_1$ and $K_2$ for calculating said pressure $P_{abd}$ inside said corporal cavity only for the next cycle in a series of cycles, and that for each cycle said control unit sets anew said constants $K_1$ and $K_2$ from the values determined in the previous cycle.

7. A device according to claim 2, characterized by the fact that said control unit determines said flow rate $Q_{ums}$ at which said control unit switches between linear and square dependency of the drop in pressure $P_{drop}$ of the flow rate as the point of intersection of said linear and said square dependency of said drop in pressure $P_{drop}$ of said flow rate Q for said respectively determined constants $K_1$, and $K_2$.

8. A device according to claim 1, characterized by the fact that said control unit generates an alarm when said flow sensor measures a value 0 of the gas flow.

9. A device according claim 1, characterized by the fact that an evacuation valve is provided for limiting said intraabdominal pressure.

10. A device according to claim 9, characterized by the fact that said evacuation valve is provided in the proximal part of an instrument inserted into said corporal cavity.

11. A device according to claim 9, characterized by the fact that, for checking the corporal pressure, said control unit closes said evacuation valve at specific time intervals.

12. A device according to claim 11, characterized by the fact that said control unit selects the magnitude of said time intervals in dependence on said pressure $P_{abd}$ inside the body.

13. A device according to claim 9, characterized by the fact that a vacuum pump is provided for enhancing evacuation performance.

14. A device according to claim 13, characterized by the fact that said control unit regulates the performance of said vacuum pump in dependence on said pressure $P_{abd}$ inside the body.

15. A device according to claim 9, characterized by the fact that said evacuation valve is a proportional valve which is regulated by said control unit in dependence on said pressure $P_{abd}$ inside the body.

16. A device according to claim 1, characterized by the fact that a heating device is provided which heats the to-be-insufflated gas to a specified temperature.

17. A device according to claim 16, characterized by the fact that said control unit sets said gas pressure and said gas flow while taking into account said specified temperature of the gas.

18. A device according to claim 1, characterized by the fact that, for insufflating the gas into said corporal cavity, an endoscopic instrument is provided on which gas pressure and gas flow sensors are disposed outside said corporeal cavity.

19. A device according to claim 18, characterized by the fact that the endoscopic instrument is a Verres needle.

20. A device according to claim 1, characterized by the fact that only one single gas supply line leads inside the body.

21. A device according to claim 1, characterized by the fact that said pressure regulator and said flow regulator are combined in one component.

* * * * *